United States Patent [19]
Yamamoto et al.

[11] Patent Number: 5,463,113
[45] Date of Patent: Oct. 31, 1995

[54] PROCESS AND APPARATUS FOR PRODUCING TEREPHTHALIC ACID

[75] Inventors: Ryoichi Yamamoto; Fujimasa Nakao; Etsurou Okamoto; Yasuhiko Yagi, all of Yamaguchi, Japan

[73] Assignee: Mitsui PetrochemicalIndustries, Ltd., Tokyo, Japan

[21] Appl. No.: 204,435

[22] Filed: Mar. 2, 1994

[30] Foreign Application Priority Data

Mar. 30, 1993 [JP] Japan ................... 5-072036

[51] Int. Cl.⁶ .................................................. C07C 51/16
[52] U.S. Cl. ........................... 562/414; 562/416; 422/211
[58] Field of Search ................................... 562/414, 416

[56] References Cited

U.S. PATENT DOCUMENTS 4,241,220  12/1980  Itaya .......................................... 562/414
5,099,064  3/1992   Huber ........................................ 562/414

FOREIGN PATENT DOCUMENTS 0461855  12/1991  European Pat. Off. .
2304255  10/1976  France .
1373230  11/1974  United Kingdom .

Primary Examiner—Michael L. Shippen
Attorney, Agent, or Firm—Birch, Stewart, Kolasch & Birch

[57] ABSTRACT

A process and an apparatus for producing terephthalic acid economically by oxidizing paraxylene supplied to an oxidizing reactor connected with a compactly designed distillation column in an acetic acid-based solvent, while effecting the distillatory recovery of the paraxylene and acetic acid efficiently without suffering from stuffing of the distillation column.

2 Claims, 3 Drawing Sheets

PRIOR ART

PROCESS AND APPARATUS FOR PRODUCING TEREPHTHALIC ACID

DISCUSSION OF RELATED ART

1. Field of the Invention

The present invention relates to a process and an apparatus for producing terephthalic acid and, in particular, for producing terephthalic acid by oxidizing paraxylene with a molecular oxygen-containing gas in a solvent based on acetic acid.

2. Background of the Invention

First, a typical conventional process for producing terephthalic acid from paraxylene is explained with reference to the appended FIG. 3 showing the flow diagram of the apparatus for such a process. The apparatus for performing the process of FIG. 3 is composed of an oxidizing reactor 1, a distillation column 2, a heat exchanger 3, a scrubber 4 for recovering the unreacted paraxylene, another scrubber 5 for recovering acetic acid, a reboiler 6 and a condenser 7.

A typical conventional process for producing terephthalic acid is based on the steps of supplying starting liquid materials, i.e. paraxylene, acetic acid as the solvent and a catalyst, including chemical components of cobalt, manganese and bromine, to the reactor 1 via a raw stock supply line 11 and introducing a molecular oxygen-containing gas via an oxygen feed line 12, in order to cause therein the oxidation of paraxylene to terephthalic acid. The resulting product of terephthalic acid is withdrawn from the reactor together with the solvent and the catalyst via a product discharge line 13 and forwarded to the isolating refinery step.

The exhaust gas from the oxidation flows, together with the vapor generated due to the reaction heat, from an oxidation exhaust line 14 into the heat exchanger 3, in which they are cooled. A part of the condensate liquid formed therein is returned to the oxidizing reactor 1 via a reflux line 15 and the remainder is forwarded to the distillation column 2 via a communication line 16. The gas is then forwarded through a communication line 17 to the paraxylene scrubber 4, where paraxylene is recovered by contacting the gas with water or with an acetic acid solution supplied thereto from a liquid supply line 19. The gas is then guided through a communication line 18 to the acetic acid scrubber 5, in which the vaporized acetic acid in the gas is recovered by contacting the gas with water or with a dilute acetic acid solution supplied thereto from a liquid supply line 20.

The gas separated from paraxylene and acetic acid is exhausted outside the system via a gas exhaustion line 21, while the paraxylene-recovered liquor is sent to the reactor 1 via a communication line 22 and the acetic acid-recovered liquor is sent to the distillation column 2 via a communication line 23.

In the distillation column 2, the acetic acid recovered liquor is distilled using the steam generated in the reboiler 6, wherein the acetic acid-enriched distillation bottom is recirculated to the reaction system through a recirculation line 24. The vapor generated in the distillation column 2 is sent to the condenser 7 via a communication line 25 and is cooled. A part of the condensate liquid formed is returned to the distillation column 2 via a reflux line 26 and the remainder is discharged out of the system as the effluent through a liquid exhaustion line 27.

While this process permits removal of the heat and water generated in the oxidizing reactor 1 to the outside of the system, a problem is left unsolved which requires complicated procedures together with an additional heat energy for recovering paraxylene and acetic acid.

It has been proposed, therefore, to solve the problem by a process which comprises supplying the exhaust gas from the oxidation of paraxylene to a distillation column directly connected to the upper part of the oxidizing reactor to effect distillation, and recirculating the distillation bottom containing paraxylene and acetic acid in a concentrated form to the oxidizing reactor, while discharging the separated water and the uncondensed gas out of the column at the top thereof (Japanese Patent Publication No. 14098/1979). For the distillation column for this process, a multi-tray column is employed. Vapor and liquid holes of such a multi-tray column are liable to be clogged or stuffed by fine particulate solid matter, such as terephthalic acid crystals in the oxidation exhaust gas. When a distillation tray of lower fractionation efficiency is used for avoiding the above problem, it becomes necessary to use as many as 100 trays for the distillatory separation of acetic acid, though paraxylene can be separated using a distillation column with about 10 trays, so that the problem of requiring of large-sized apparatus occurs.

Use of a packed column with packings exhibiting high fractionation efficiencies, for example, structured packings, in place of a multi-tray distillation column also suffers from stuffing of the packed bed by the finely dispersed solid crystals, and thus, a decrease in the performance of the distillation. The complicated structure of the dendroidal multitubular distributor will add a further cost problem.

SUMMARY OF THE INVENTION

An object of the present invention is to solve the problems encountered in the conventional technique and to provide a process which can afford to produce terephthalic acid economically by oxidizing paraxylene in an acetic acid-based solvent using an oxidizing reactor connected to a compact distillation column, while effecting the distillatory recovery of the paraxylene and acetic acid efficiently without suffering from stuffing of the distillation column.

Another object of the present invention is to provide a compactly designed low cost apparatus adapted for realizing the above-mentioned process for producing terephthalic acid efficiently.

Thus, in the present invention, terephthalic acid is produced by supplying paraxylene and a molecular oxygen-containing gas to an oxidizing reactor connected to a distillation column having at the lower part thereof a solid matter collecting tray and at the upper part thereof a packed bed, in order to cause oxidation of the paraxylene in a solvent based on acetic acid in the presence of a catalyst to form terephthalic acid, introducing the oxidation exhaust gas into the distillation column and collecting finely dispersed solid matters by means of the solid matter collecting tray, and effecting distillation of substances contained in the oxidation exhaust gas through the packed bed, while removing heat and water out of the distillation column and recirculating the separated paraxylene and acetic acid to the oxidizing reactor.

The apparatus for producing terephthalic acid according to the present invention comprises an oxidizing reactor for oxidizing paraxylene supplied thereto with a molecular oxygen-containing gas in a solvent based on acetic acid in the presence of a catalyst to form terephthalic acid and a distillation column connected to the upper part of the oxidizing reactor and having at its lower part a solid matter collecting tray and at its upper part a packed bed.

DETAILED DESCRIPTION OF THE INVENTION

Figure 1:
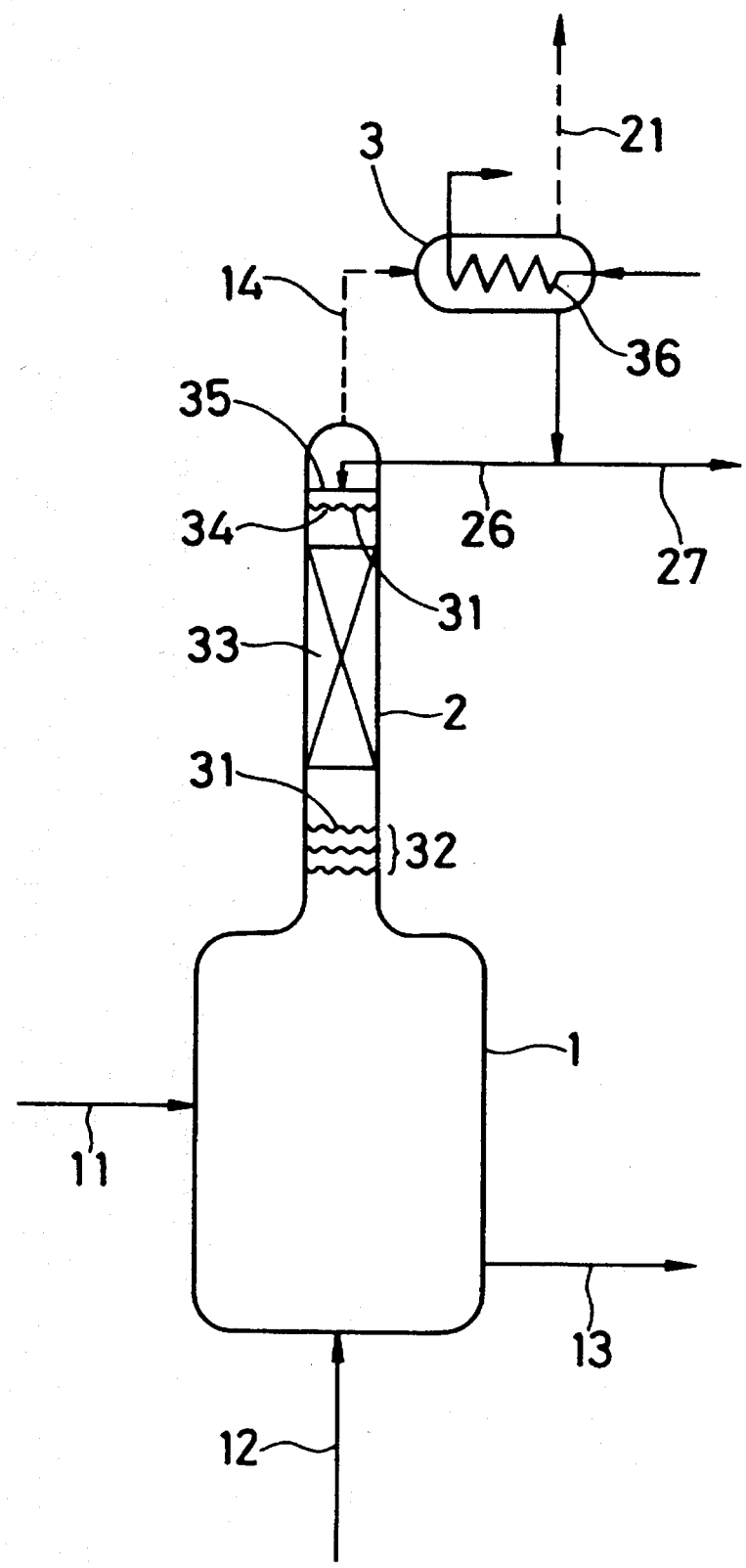
FIG. 1 is a flow sheet of the apparatus for producing terephthalic acid according to a preferred embodiment of the present invention.

According to the present invention, the oxidizing reactor is constructed so as to effect a liquid phase oxidation of paraxylene in a solvent based on acetic acid in the presence of a catalyst to form terephthalic acid. The starting paraxylene may be supplied to the reactor as a solution in acetic acid or the both are supplied thereto each separately.

As the catalyst, any conventionally known one can be used, for example, an oxidation catalyst composed of cobalt, manganese and bromine, an oxidation catalyst containing a further metal component in addition, to and so on. In general, the catalyst is introduced into the reactor together with the solvent.

For the molecular oxygen-containing gas, for example, oxygen gas, a gas mixture containing oxygen and nitrogen or carbon dioxide or the atmospheric air may be employed. The molecular oxygen-containing gas is supplied to the reactor by blowing it into the reaction liquid mixture from outside of the system.

To the upper part of the reactor, a distillation column is connected, by which the reaction heat and the reaction water generated in the reactor are removed to the exterior of the system. The distillation column may be connected to the reactor directly using a pipe or it may be joined at its lower end, bodily with the reactor top, without using a pipe.

The distillation column is provided in its lower part with a solid matter collecting tray for removing fine particulate solid matter in the gas phase and in its upper part with a packed bed or a layer of packing for distillatory separation of water from paraxylene and acetic acid. Here, it is preferable to employ a liquid distributing tray as a liquid distributor to be disposed above the packed bed or as a liquid re-distributor to be disposed at an intermediate portion of the packed bed.

The solid matter collecting tray may be one which can collect fine solid matter and even such one that exhibits a lower fractionation efficiency may be used. For such a tray, one with or without a downcomer may be used. The number of trays to be employed may differ in accordance with the structure and efficiency of each specific tray and, in general, one or more, preferably 2–5 may be adequate.

The packed bed is only for the distillatory separation of water from paraxylene and acetic acid and it is preferable to use packing exhibiting a higher liquid/gas contacting efficiency. For such a packing, there may be employed, for example, a structured packing, such as a sheet type structured packing, gauze type structured packing or a formed structured packing, a random packing, such as a lamellar random packing, a gauze type random packing, an annular random packing and a saddle-like random packing. For the specific surface area of the packing, a value in the range of 50–1500 $m^2/m^3$, preferably in the range of 100–1000 $m^2/m^3$ may be adequate. In case of using a metallic sheet type structured packing, one which has a specific surface area in the range of 50–1000 $m^2/m^3$, preferably in the range of 100–750 $m^2/m^3$ may be suitable. In case of using a metallic gauze type structured packing, one which has a specific surface area in the range of 100–1500 $m^2/m^3$, preferably in the range of 100–1000 $m^2/m^3$ may be adequate.

The liquid distributing tray for use as the liquid distributor disposed above the packed bed or as the liquid re-distributor disposed at an intermediate portion of the packed bed is for distributing the liquid uniformly over the area of the packed bed and therefor is employed one having no downcomer. For this tray, it is sufficient usually to use a single tray, though multiple trays may be employed. This tray may preferably, so long as it has a large diameter of at least 30 cm, be furnished with partition plates disposed, for example, radially on the upper face thereof to facilitate a uniform distribution of the liquid.

As the trays for the solid matter collector to be disposed in the lower part of the distillation column and as the liquid distribution trays for the liquid distributor and for the liquid re-distributor to be incorporated in the upper part of the column, either identical ones or different ones may be used. For the tray which is devoid of a downcomer to be used, there may be enumerated, for example, a perforated ripple plate tray, a flat perforated plate tray and a multi-rod tray. For the tray which has a downcomer, there may be enumerated, for example, a perforated plate tray, a bubble-cup tray and a valve tray, all of which are provided with a downcomer.

For these trays, a perforated ripple plate is preferred. The perforated ripple plate is a tray constituted of a ripple plate with many perforations arranged uniformly over the plate. A perforated ripple plate having perforations of from 200 to 200,000 per square meter, preferably from 200 to 50,000 per square meter with a pore diameter of from 0.2 to 100 mm, preferably from 3 to 20 mm, and a ripple pitch, namely, a corrugation ruffle interval of from 5 to 500 mm, preferably from 10 to 150 mm, is preferred, with a preferable distance between the trays in the range of from 20 to 200 cm, preferably from 30 to 70 cm. It is preferable to provide the tray with partition plates for subdividing its surface area, in order to prevent any bias flow of vapor and liquid due to a possible inclination of the apparatus, etc. In case of piling up of a plurality of ripple plates in several overlaps, it is preferable to lay one ripple plate over another so as to cross their directions of the corrugation riffles with each other.

For producing terephthalic acid using the apparatus according to the present invention, paraxylene is supplied to the oxidizing reactor and is oxidized here with a molecular oxygen-containing gas in a solvent based on acetic acid at a temperature of 150° –270° C. under a pressure of 5–20 $Kg/cm^2$ gauge, in the presence of a catalyst to form terephthalic acid. The oxidation exhaust gas, namely, the exhaust gas from the oxidizing reactor, containing the vapors of water and acetic acid generated is sent to the distillation column, where it is subjected to a rectification to separate water from the paraxylene and acetic acid, wherein the heat and water generated in the reactor are taken out of the system and the unreacted paraxylene and acetic acid thus separated are returned to the oxidizing reactor. By the removal of water and heat, a high quality terephthalic acid can be produced at a high yield.

It is preferable to choose a proportion of paraxylene relative to the acetic acid used as the solvent therefor of 1–50% by weight. When a catalyst containing cobalt, manganese and bromine is used, the amount of the catalyst used may preferably be in the range of from 10 to 5000 ppm of cobalt as its atomic weight, from 10 to 5000 ppm of manganese as its atomic weight and from 10 to 10000 ppm of bromine as its atomic weight, based on the weight of the solvent.

When the atmospheric air is used as the molecular oxygen-containing gas, it is used preferably in a proportion of 0.5–15 $Nm^3$ per 1 kg of paraxylene.

In the distillation column, the distillation takes place under the utilization of the heat content of the oxidation exhaust gas entering therein from the oxidizing reactor, wherein the heat and reaction water generated in the oxidizing reactor are removed out of the system and the unreacted paraxylene and acetic acid are recovered. The oxidation exhaust gas is first subjected to the removal of fine particulate matter of terephthalic acid, etc. upon passing through the solid matter collecting tray at the lower portion of the distillation column, whereby stuffing of the packed bed due to adhesion of solid matter thereto is prevented and fine particulate terephthalic acid, etc. are recovered.

The oxidation exhaust gas passes next through the packed bed, where it is subjected to a fractional distillation to separate water from paraxylene and acetic acid. In general, a fractional separation of water and acetic acid is difficult, since their boiling points are close to each other. However, they can be fractionally separated easily by using a packing having a high gas/liquid contacting efficiency in the packed bed. Here, paraxylene and acetic acid are concentrated on the side of liquid phase and are returned from the bottom of the distillation column to the oxidizing reactor together with the fine particulate solid matter collected on the solid matter collecting tray disposed beneath the packed bed.

The water which is fractionally separated in the packed bed, namely water vapor, is cooled in a heat exchanger to form a condensate, as in the conventional technique, from which a part of the condensate water is refluxed to the distillation column. By refluxing the condensate water to the liquid distributing tray, a uniform distribution of the reflux water over the packed bed and, thus, an increased distillation efficiency can be achieved.

The distillation operation in the distillation column encompasses also the recovery operations for paraxylene and acetic acid realized in the separate scrubbers in the conventional technique. It realizes the distillation by utilizing only the heat generated in the oxidizing reactor without supplying any heat from the outside while preventing occurrence of stuffing of the packed bed, so that it contributes to an increase in the oxidation reaction yield together with an efficient recovery of paraxylene, acetic acid, and finely dispersed solids of terephthalic acid etc.

As detailed above, the process for producing terephthalic acid according to the present invention can afford to produce terephthalic acid at a lower cost by effecting the fractional distillation of paraxylene, acetic acid and water efficiently to recover them without suffering from occurrence of stuffing of the distillation column, by using an oxidizing reactor connected to a compact distillation column, which is provided in its lower part with a solid matter collecting tray and in its upper part with a packed bed.

The apparatus for producing terephthalic acid according to the present invention is compact and low priced due to its construction as described above and permits operating without suffering from the occurrence of clogging or stuffing of the distillation column and is adapted to produce terephthalic acid efficiently.

Below, the present invention is explained in a further detail by a preferred embodiment.

Figure 3:
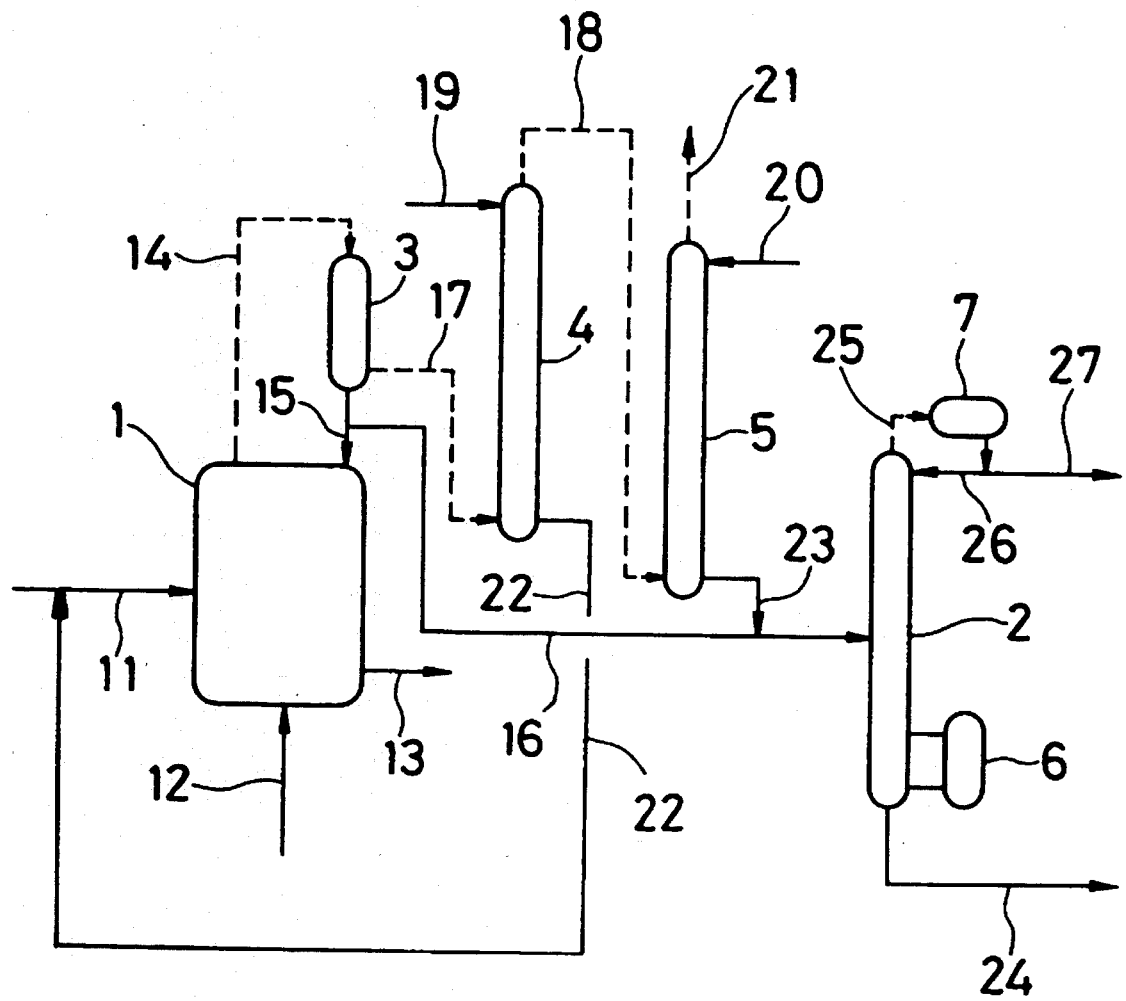
FIG. 3 is a flow sheet of a typical conventional apparatus for producing terephthalic acid.

In FIG. 1, a flow sheet for an apparatus for producing terephthalic acid of one embodiment of the present invention is given, in which the elements and the constituent parts corresponding to those of FIG. 3 are indicated by the same numeral symbols as in FIG. 3.

In the embodiment of FIG. 1, the apparatus is constructed in such a manner that the starting paraxylene, acetic acid as the solvent and the catalyst are supplied to the oxidizing reactor 1 via a raw stock supply line 11 and the molecular oxygen-containing gas is fed thereto via an oxygen feed line 12 to cause the oxidation of paraxylene into terephthalic acid.

Above the oxidizing reactor 1, a distillation column 2 is connected integrally therewith. Inside the distillation column 2, there is provided in its lower part a solid matter collecting tray 32 composed of a plurality of stages of perforated ripple plates 31 and, above it, with a packed bed 33 and further, still above this, with a liquid distribution tray 34 composed of a perforated ripple plate 31.

As the perforated ripple plates 31 for the solid matter collecting tray 32 and for the liquid distribution tray 34, identical trays 31 are employed. In the solid matter collecting tray 32, a plurality of perforated ripple plates 31 are superposed in such a manner that the directions of corrugation ruffles for these plates cross with each other. On the perforated ripple plate 31 for the liquid distribution tray 34, partition plates 35 are disposed extending radially from the center. In the packed bed 33, many pieces of sheet type structured packing 40, as shown in FIG. 2, are packed.

The distillation column 2 is connected at its top to a heat exchanger 3 having a water tube cooling element 36 through a gas exhaustion line 14. The heat exchanger 3 is connected at its upper portion with a gas exhaustion line 21 and at its lower portion with a reflux line 26 which communicates to the distillation column 2 at a portion above the liquid distribution tray 34, and is branched on the way thereto to a liquid exhaustion line 27.

Figure 2:
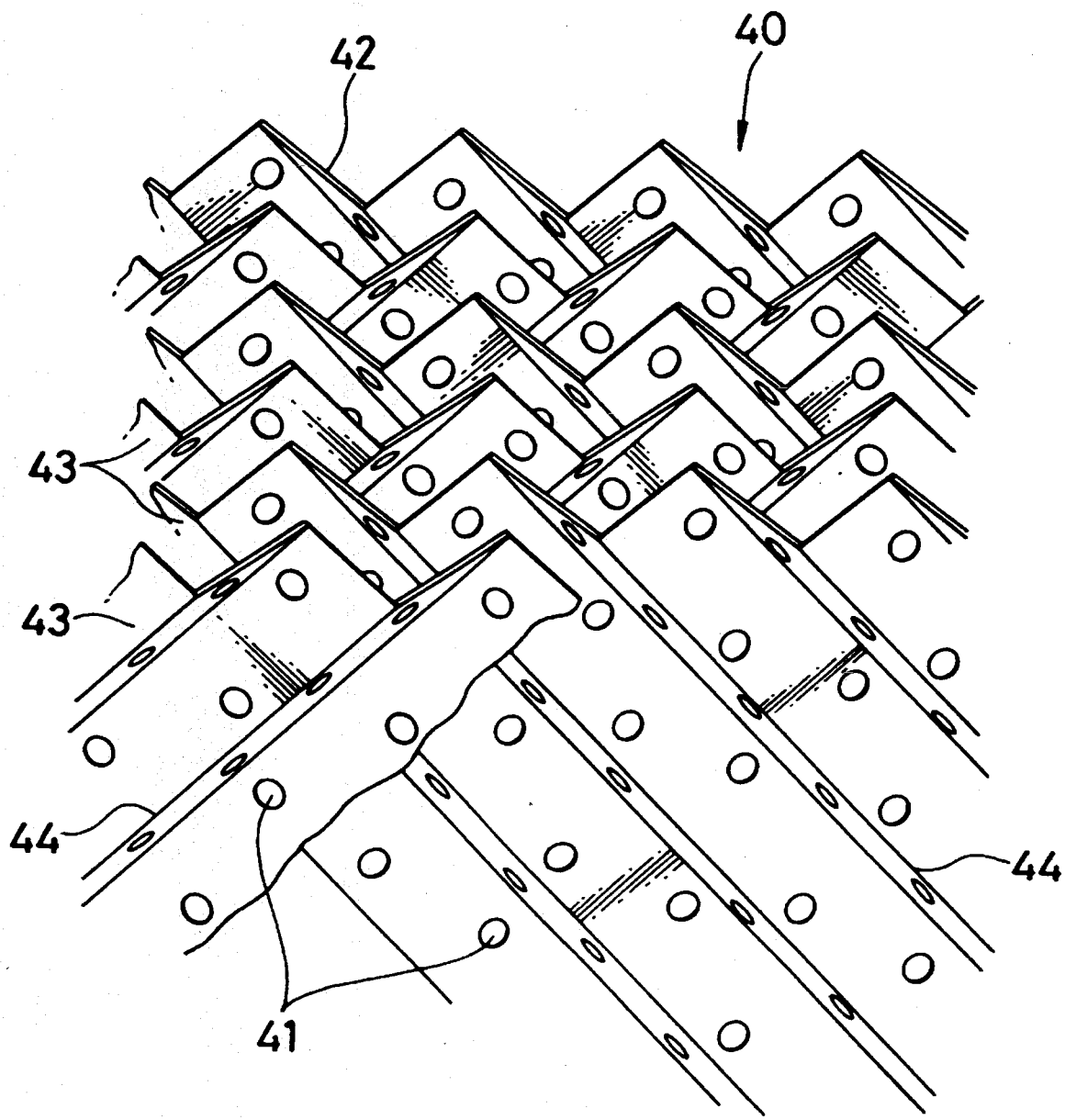
FIG. 2 illustrates the structure of the multi-lamellar structured packing as used in the embodiment in a perspective view.

The sheet type structured packing 40 has, as shown in FIG. 2 in a partial cutout perspective view, a construction in which a plurality of perpendicularly extending perforated sharp-edged ripple plates 43 having many perforations 41 and triangular corrugation 42 with parallel sharp ridges 44, are bonded to each other in such a manner that they are disposed parallel with the ridges 44 of two neighboring ripple plates 43 inclining at an angle of inclination of about 45° in directions crossing rectangularly with each other.

In the production of terephthalic acid by means of the above-described apparatus, the starting materials, namely, paraxylene, acetic acid as the solvent and a catalyst containing cobalt, manganese and bromine, are supplied to the oxidizing reactor 1 via a raw stock supply line 11, while feeding thereto a molecular oxygen-containing gas via an oxygen feed line 12, to cause oxidation of paraxylene into terephthalic acid. The so-produced terephthalic acid is conducted to an isolating refinery step together with the solvent and the catalyst via a product discharge line 13.

The oxidation exhaust gas from the oxidizing reactor 1 enters then into the distillation column 2 together with the vapor generated by the liberated reaction heat. Here, the distillation is carried out by making use of the heat content in the oxidation exhaust gas and the vapor conducted from the oxidizing reactor 1, whereby the heat and the water generated in the oxidizing reactor 1 are removed out of the system and the unreacted paraxylene and acetic acid are recovered.

The oxidation exhaust gas introduced into the distillation column 2 is first subjected to a removal of fine particulate solid matters, such as terephthalic acid crystals, upon passing through the solid matter collecting tray 32 in the lower part of the column 2.

On the solid matter collecting tray 32, the fine solid particles of terephthalic acid, etc. are collected upon contact of the gas phase consisting of the oxidation exhaust gas and of the vapor flowing up through the perforations in the piled perforated ripple plates 31 with the liquid phase of concentrated solution flowing down through also the perforations of the perforated ripple plates 31. Thereby a stuffing of the column due to adhesion of fine particulate solid matter onto the surfaces of the packing in the packed bed 33 is prevented, and fine particles of solid matter of terephthalic acid, etc. are recovered.

The oxidation exhaust gas having passed the perforated ripple plates 31 of the solid matter collecting tray 32 is then subjected to a distillatory fractional separation of water from paraxylene and acetic acid upon passing through the packed bed 33. The packings in the packed bed 33 have a large specific surface area, so that they reveal a high gas/liquid contact efficiency, resulting in an efficient fractionation of water, paraxylene and acetic acid.

Paraxylene and acetic acid are fractionated in the packed bed 33 and concentrated progressively in the liquid phase and are then returned to the oxidizing reactor 1 from the bottom of the distillation column 2 together with the fine particulate solid matter collected in the solid matter collecting tray 32. Here, a portion of water is also returned to the reactor 1 so as to maintain the water content in the reactor 1 at a value of 0.5–15% by weight.

The oxidation exhaust gas having passed through the packed bed 33 and thus containing the uncondensed water vapor enters then into a heat exchanger 3 via an oxidation exhaust line 14 and is cooled here by a cooling water in a water tube cooler 36 to condense the vapor, while the non-condensing components of the gas are exhausted out via a gas exhaustion line 21. A part of the condensed water is returned to the distillation column 2 via a reflux line 26.

Here, the reflux water is distributed uniformly over the packed bed 33 by flowing on a liquid distributing tray 34 radially from the center thereof by an assistance of partition plates 35 disposed on the liquid distributing tray 34, in order to improve the fractionation efficiency. A part of the condensate water is discharged out of the system as the effluent via a liquid exhaustion line 27. In this manner, the heat and the water generated in the oxidizing reactor 1 are taken out of the system. The ratio of the amount of the discharged condensate water to the amount of the returned condensate water, namely, the reflux ratio, may preferably be in the range from 20:1 to 3:1.

Thus, the conventional process steps of the recovery of paraxylene and acetic acid realized using the scrubbers 4 and 5 and the distillation realized in the distillation column 2 in the prior art process are carried out simultaneously in the newly designed distillation column 2. Here, the distillation in the new distillation column 2 is realized by making use of the heat generated in the oxidizing reactor 1 without necessitating any heat input from other source, so that an effective heat utilization is attained. In addition, an efficient recovery of paraxylene and acetic acid as well as fine particulate solid matter, such as terephthalic acid, etc., can be realized while preventing stuffing of the apparatus, so that the efficiency of the oxidizing reaction is improved and the production of terephthalic acid can be effected at a lower cost.

While the apparatus shown in FIG. 1 is constructed by an integral connection of the oxidizing reactor 1 and the distillation column 2, it is possible to construct by connecting separately arranged ones using suitable means, such as connection pipes. Also, it is possible to integrate the distillation column 2 and the heat exchanger 3, though they are separately disposed in the apparatus explained above. Further, the perforated ripple plate 31 for the solid matter collecting tray 32 and the liquid distributing tray 34 and the packings filled in the packed bed 33 may not be restricted only to those explained above.

Below, test results are explained.

EXAMPLES

Example 1

An apparatus as shown in FIG. 1 was employed, in which three perforated ripple plates 31 were piled one over another as the solid matter collecting tray 32, above which sheet type structured packing is filled as the packed bed 33, on which a single perforated ripple plate 31 was placed as the liquid distributing tray 34.

The perforated ripple plate 31 had its corrugation riffles at a ruffles interval of 40 mm and perforations with a diameter of 6 mm at a perforation density of $7000/m^2$, wherein the piling of such plates was realized at a plate distance of 40 cm, so as to cross the direction of the corrugation ruffles of two neighboring ripple plates rectangularly with each other. The sheet type structured packing had, as shown in FIG. 2 in a partial cutout perspective view, a construction in which a plurality of perpendicularly extending perforated triangularly sharp-edged ripple plates are disposed parallel with the ridges of two neighboring ripple plates inclining at an angle of inclination of about 45° in directions crossing rectangularly with each other. The specific surface area and the height of the packed bed were found to be $250\ m^2/m^3$ and 5 m respectively.

To the oxidizing reactor 1 of the apparatus explained above (which had, however, no partition plate 35), paraxylene, acetic acid and the catalyst were supplied via the raw stock supply line 11 while feeding thereto the atmospheric air via the oxygen feed line 12, whereupon the oxidation and the distillation were carried out at a reaction temperature of 190° C. under a pressure in the oxidizing reactor 1 and in the distillation column 2 of 10 $Kg/cm^2$ gauge at a reflux ratio of the distillation column 2 of 10 to produce terephthalic acid. The concentration of acetic acid in the effluent discharged from the liquid exhaustion line 27 was found to be 15 wt.-%.

Example 2

The test was carried out under the same conditions as in Example 1, except that partition plates 35 having a form of a cross were disposed radially on the upper face of the liquid distributing tray 34, wherein it was found that the acetic acid concentration in the effluent was changed to 10% by weight.

Example 3

The test was carried out under the same condition as in Example 1, except that the height of the packed bed 33 was altered to 20 m and a liquid re-distributing tray similar to the liquid distributing tray 34 was disposed at an intermediate portion, wherein it was found that the acetic acid concentration in the effluent was changed to below 1% by weight.

Comparative Example 1

The test was conducted under the same condition as in Example 1, except that perforated ripple plates 31 were piled up to the same height in the place of the packed bed 33, wherein it was found that the acetic acid concentration in the effluent was changed to 60% by weight.

Comparative Example 2

The test was conducted under the same condition as in Example 1, except that sheet type structured packings were employed instead of the solid matter collecting tray 32, wherein it was found that powdery solid matters were adhered to the packed bed at its lower part and the distillation efficiency was lowered, before the apparatus became subsequently inoperable.

Example 4

The test was carried out under the same condition as in Example 1, except that a dendritic multitubular distributor was employed instead of the liquid distributing tray 34, wherein it was found that the acetic acid concentration in the effluent was changed to 20% by weight.

We claim:

1. A process for producing terephthalic acid by oxidizing paraxylene with a molecular oxygen-containing gas, comprising supplying paraxylene and a molecular oxygen-containing as to an oxidizing reactor connected to a distillation column having at the lower part thereof a solid matter collecting tray and at the upper part thereof a packed bed, in order to cause oxidation of the paraxylene in a solvent based on acetic acid in the presence of a catalyst to form terephthalic acid, introducing the oxidation exhaust gas into the distillation column and collecting finely dispersed solid matter by means of the solid matter collecting tray, effecting distillation of substances contained in the oxidation exhaust gas through the packed bed, while removing heat and water out of the distillation column, and recirculating the separated paraxylene and acetic acid to the oxidizing reactor.

2. A process as in claim 1, wherein the distillation column is provided above the packed bed with a liquid distribution tray devoid of downcomer, and wherein the oxidation exhaust gas which has left overhead the distribution tray is cooled by a heat exchanger and part of the condensate formed is returned to the distribution tray.

* * * * *

UNITED STATES PATENT AND TRADEMARK OFFICE
CERTIFICATE OF CORRECTION

PATENT NO. : 5,463,113
DATED : Oct. 31, 1995
INVENTOR(S) : Yamamoto et al.

It is certified that error appears in the above-indentified patent and that said Letters Patent is hereby corrected as shown below:

Column 10,
Claim 1, line 5, change "as" to --gas--.

Signed and Sealed this

Twenty-eighth Day of January, 1997

Attest:

BRUCE LEHMAN

Attesting Officer     Commissioner of Patents and Trademarks